United States Patent [19]
Cole

[11] Patent Number: 6,058,779
[45] Date of Patent: May 9, 2000

[54] COUPLED DIAPHRAGM INTERFACE FOR PHACOEMULSIFICATION APPARATUS

[76] Inventor: Mark S. Cole, 21251 Hillgate Cir., Trabuco Canyon, Calif. 92679

[21] Appl. No.: 09/247,841

[22] Filed: Feb. 10, 1999

[51] Int. Cl.[7] ........................................ G01L 7/08
[52] U.S. Cl. ............................................... 73/715
[58] Field of Search ............................. 73/715, 716, 717, 73/720, 721, 722, 726, 727, 728

[56] References Cited

U.S. PATENT DOCUMENTS 5,392,653   2/1995   Zanger et al. .......................... 73/756

Primary Examiner—William Oen
Attorney, Agent, or Firm—Walter A. Hackler

[57] ABSTRACT

The pressure measurement system includes a diaphragm having a first and a second side and a chamber for exposing the diaphragm first side to a fluid. A force transducer is utilized for measuring force exerted by the fluid on the diaphragm first side. A plate and a captive portion of the diaphragm extending from the second side thereof and partially encasing a portion of the plate enables the plate to be secured to the force transducer with the use of a ferromagnetic plate and a magnet attached to the force transducer, the force transducer may be removably engaged with the plate.

20 Claims, 2 Drawing Sheets

COUPLED DIAPHRAGM INTERFACE FOR PHACOEMULSIFICATION APPARATUS

The present invention generally relates to a pressure measurement system and more particularly is related to a pressure monitoring system for ophthalmic instruments such as a Phaco instrument for removing the crystalline lens from an eye.

Typically, cataracts, or crystalline manifestations, in an eye are removed by fragmentation thereof which may include an ultrasound driven hollow needle inserted into the eye through a small incision in the sclera. Removal of the fragmented lens is effected through a center hole in the needle and involves continuous circulation of fluid through the eye which is provided by the hollow needle inserted therein.

While eye pressure must be carefully maintained to prevent collapse of the eye chamber, over-pressure may be necessary at times to remove a blockage in the hollow needle which may be caused by a fragmented lens. In addition, fluid flow in the needle may be reversed to reflux the fluid and dislodge the fragmented lens from the hollow needle. During this operation, it is, of course, necessary to monitor and maintain eye pressure preselected absolute maximum level.

Failure to measure and control fluid pressure during the removal process may result in the formation of a large void in the plastic tubing system leading from the needle to a pump utilized in providing the fluid circulation. In addition, a sudden release of blockage could result in the reduction of pressure in the eye as the void is filled by the liquid from the eye which may not be replaced with sufficient speed, thereby resulting in the collapse of the cornea as hereinabove pointed out.

Conversely, if there is poor control during the reflux process, a large over-pressure may be generated in the eye which would cause inflation of the eye when the blockage breaks free.

A number of peristaltic pumps have been developed for use with Phaco instruments such as described in U.S. Pat. No. 5,230,614, entitled "Reduced Pulsation Tapered Ramp Pump Head," assigned to the assignee of the present application. This above-referenced patent is incorporated herein by specific reference thereto.

Heretofore, pressure measurement systems, utilizing a diaphragm for the isolated measurement of pneumatic or hydraulic pressure, have incorporated the diaphragm in a number of different structural configurations.

Such systems are discussed in U.S. Pat. No. 5,392,653, entitled "Pressure Transducer Magnetically-Coupled Interface Complementing Minimal Diaphragm Movement During Operation", which is incorporated herein in its entirety by this specific reference thereto.

SUMMARY OF THE INVENTION

In accordance with the present invention, the pressure measurement system generally includes a diaphragm having a first side and a second side along with a chamber which provides a means for exposing the diaphragm first side to a fluid.

The force transducer provides a means for measuring force exerted by the fluid on the diaphragm first side. In one embodiment of the present invention, means for removably coupling the force transducer means to the diaphragm second side includes a ferromagnetic plate and means, extending from the diaphragm second side, for at least partially encasing a portion of the ferromagnetic plate in order to secure the plate to the diaphragm second side.

In addition, a magnet, attached to the force transducer means, provides a means for removably engaging the ferromagnetic plate and accordingly, coupling the plate and diaphragm to the force transducer.

In another embodiment of the present invention, the means for removably coupling the force transducer to the diaphragm second side includes a plate and means extending from the diaphragm second side for at least partially encasing a portion of the plate in order to secure the plate against the diaphragm second side.

Latching means are provided and disposed on the plate for removably engaging the force transducer and accordingly coupling the diaphragm and plate thereto.

More particularly, the means extending from the diaphragm comprises a captive portion mold into the diaphragm second side. The captive portion is centered in the diaphragm second side with a surrounding resilient ring which enables a diaphragm movement in response to a change in the force exerted on the diaphragm first side.

Still more particularly, the captive portion hereinabove referenced, may include a ring disposed in a spaced apart relationship with a center of the diaphragm second side and the plate includes a groove disposed in a perimeter of the plate which provides a means for accepting the ring. The plate is firmly supported against the diaphragm means center second side by the ring. In addition, this structure significantly increases the tinsil strength of the plate/diaphragm interface over prior art devices such as shown and described in the hereinabove referenced U.S. Pat. No. 5,392,653.

Shoulder means, formed into a perimeter of the diaphragm means, provides a means for both sealing the diaphragm means to the chamber and, in addition, tensioning the diaphragm means over an open end of the chamber. This greater tension allows for less hysteresis at the transition between the compression and tension loading of the diaphragm coupling. The benefit of this feature is that an associated vacuum monitoring system has less compliance and the overall phaco system is enhanced. That is, the vacuum rise time is faster and there is less surge after an occlusion clearance.

The diaphragm shoulder allows self-sealing of the diaphragm to the chamber without the need for a tightly compressed retainer as was necessary in the prior art. Further, no bonding of the plate is required to the diaphragm and accordingly the plate is less susceptible to the effects of a corrosive environment. Thus, the pressure measuring system, or device, of the present invention is reusable.

The present invention also encompasses an improvement in a system such as described in U.S. Pat. No. 5,392,653. This improvement includes a plate and, as hereinabove described, a means, extending from the diaphragm second side, for at least partially encasing a portion of the plate in order to secure the plate to the diaphragm along with a latching means disposed on the plate for removably engaging the force transducer or, in the case of a ferromagnetic plate, a magnet for coupling the force transducer to the plate.

BRIEF DESCRIPTION OF THE DRAWINGS

The advantages and features of the present invention will be better understood by the following description when considered in conjunction with the accompanying drawings, in which.

DETAILED DESCRIPTION OF THE DRAWINGS

Figure 1:
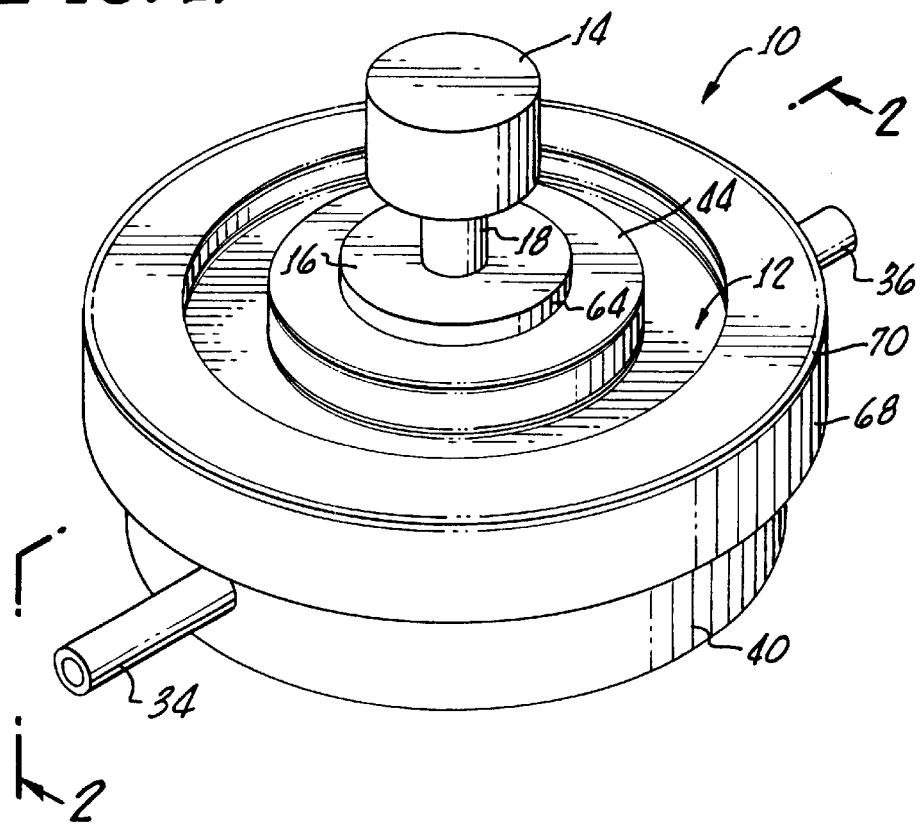
FIG. 1 is a perspective view of the pressure measurement system in accordance with the present invention generally showing a chamber, a diaphragm, force transistor and magnet system for coupling the force transistor to the diaphragm.
Figure 2:
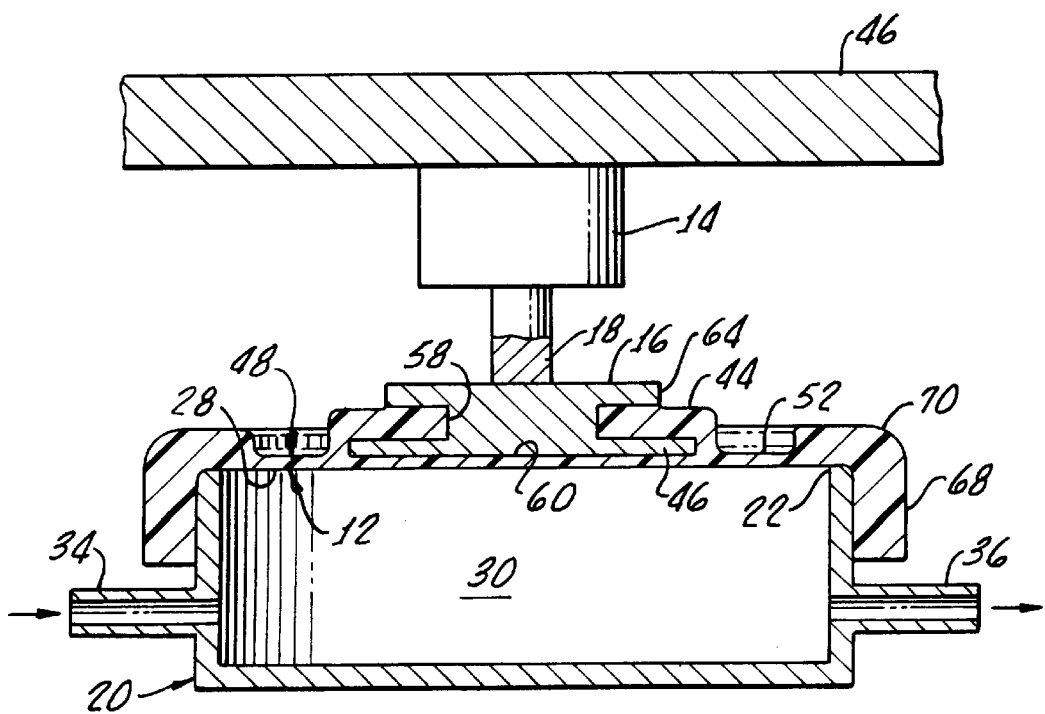
FIG. 2 is a cross sectional view taken along the section 2—2 of FIG. 1.

With reference to FIGS. 1 and 2, there is shown a pressure measurement system 10 in accordance with the present invention generally showing a diaphragm 12, a force transducer 14, a ferromagnetic plate 16, a magnet 18, and a chamber 20.

The chamber 20 may be formed from any suitable material and may have, for specific example, a diameter of about one inch, and an open end 22 for exposing a diaphragm first side 28 to a fluid (not shown) disposed in an inside 30 of the chamber 20.

In providing a means for exposing the first side 28 of the diaphragm 12 to the fluid, the chamber 20 includes a fluid inlet 34 and an outlet 36 disposed in opposing positions in a curved portion 40 of the chamber 20.

The magnet 18 is permanently attached to the transducer 14 and may be of any suitable type, either electromagnetic or permanent magnet. If an electrical magnet is used, suitable coupling, by means of wires (not shown), to a control unit (not shown), may be utilized for interrupting the current flow to the electrical magnet, thus decreasing, or eliminating, the magnetic coupling to the plate 16 for enabling separation of the magnet 18 and the transducer 14 from the plate 16.

The transducer 14 in turn is attached to a member 46 within a control console (not shown) or the like.

The separability of the transducer from the plate 16 and the chamber 20 enables the chamber 20 and plate 16 and diaphragm 12 to be autoclived, or otherwise sterilized, without affecting the transducer 14 and from the magnet 18. After sterilization, the transducer 14 and magnet 18 may be recoupled to the plate 16. Alternatively, in a disposable system, a replacement chamber and/or plate 16/diaphragm 12 may be coupled to the transducer 14 via the ferromagnetic plate 18 as hereinabove described.

A captive portion 44, molded as part of the diaphragm 12 and extending therefrom, provides a means for at least partially encasing a portion 46 of the plate 16 in order to secure the plate 16 to a diaphragm second side 48.

Thus, the combination of the ferromagnetic plate 16, the captive portion 44 of the diaphragm 12 and the magnet 18 together provide a means for removably coupling the force transducer 14 to the diaphragm second side 48.

More particularly, the captive portion 44 is centered in the diaphragm 12 with a surrounding resilient ring 52 which provides a means for enabling diaphragm movement in response to a change in the force exerted on the diaphragm first side 28.

As shown in the FIGS. 1 and 2, the captive portion 44 includes a ring 58 disposed in a spaced apart relationship with a diaphragm center 60. The plate 16 includes a groove 62 in a perimeter 64 for accepting the ring 58. The ring 58 and groove 60 are sized for enabling the plate 16 to be firmly supported against the diaphragm second side center 60. This structure enables the securing of the plate 16 to the diaphragm 12 without the use of bonding.

Preferably, the plate is of a geometry, as shown in the Figures, which enables insert molding into the diaphragm without a bonding agent or separate process. This provides an economic advantage in the manufacture of the system 10.

In addition, because no bonding is necessary, no surface preparation is required and accordingly the plate 16 is less susceptible to any effects of a corrosive environment. This structure contributes to the reusability of the system, or device 10.

The diaphragm 12 may be formed of any suitable material; however, it is expected that it would be formed from a thin silicon material, for example, about 13 mils thick in the diaphragm ring 52. This enables a free movement of the diaphragm in response to pressure fluid within the chamber 20. Because the transducer 14 responds only to force exerted by the diaphragm thereon, through the magnet 18, the exact position of the diaphragm 12 with respect to the opening 22 and remaining chamber interior 30, is not important in operation of the device. This is a significant improvement of prior art devices which are based on displacement of a diaphragm to measure pressure.

Another feature of the present invention is a shoulder 68 formed into a perimeter 70 of the diaphragm 12 which provides a means for both sealing the diaphragm 12 to the chamber 20 as well as for tensioning the diaphragm 12 over the open end 22 of the chamber 20.

This structure provides significant advantage of the prior art in that the diaphragm is self-sealing without the need for any additional clamps or retainers for compressing the diaphragm 12 against the chamber 20. As hereinabove noted, placing a diaphragm in tension with a lateral side load applied thereto, allows for less hysteresis at the transition between the compression and tension loading of the diaphragm coupling. The tension is provided by forming the diaphragm 12 within the inside diameter of the shoulder 68 being slightly smaller than an outside diameter of the chamber 20.

Figure 3:
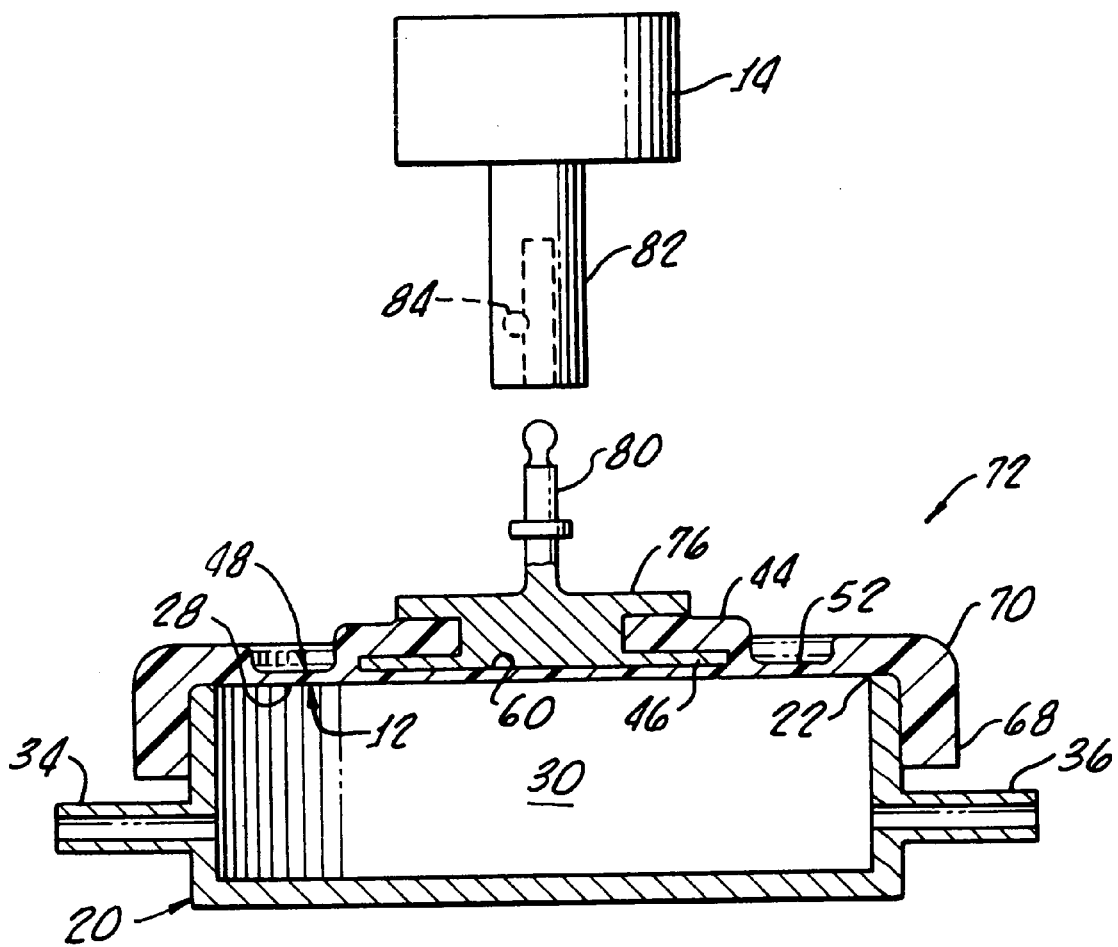
FIG. 3 is an alternative embodiment of the present invention utilizing a plate and the latching means for removably coupling the plate to a force transducer.

With reference now to FIG. 3, there is shown an alternative embodiment 72 of the present invention. It should be appreciated that common reference characters enumerated in FIG. 3 refer to identical or similar structure hereinabove described in connection with the embodiment 10 of the present invention.

The system 72 utilizes a plate 76 similar to the plate 16 hereinabove described in FIGS. 1 and 2, but further including a fitting 80 which provides, in combination with a socket 82 attached to the transducer 14, latching means for removably engaging the plate 76 to the transducer 14. A set screw 84 or any suitable releasable clamping device may be utilized for releasably coupling the fitting 80 with the socket 82. The remaining structure and function of the embodiment 72 is identical with that of embodiment 10, hereinabove described.

Both embodiments 10, 72 in accordance with the present invention provide a method of measuring pressure through the use of a forced transducer 14 which basically allows the diaphragm 12 to remain substantially stationary. That is, there are no position measurement requirements necessary as in prior art systems.

In addition, the non-sterile second side 48 of the diaphragm 12 is free from pneumatic or hydraulic contact as is the case with many prior art systems involving a secondary closed pneumatic or hydraulic system.

By way of example, the force transducer 14 may be a strain gauge, which is not subject to mechanical overload, and inherently remains stable for long periods of time.

With proper selection of diaphragm and transducer, the system can measure pressures both greater or less than the atmospheric pressure, and saturation will not occur if the force transducer 14 is sealed.

Because the diaphragm 12 is uniformly supported and sealed across the opening 22 of the chamber 20, the resilient nature of the silicon diaphragm 12 will automatically center within the opening 22 which eliminates any long term drift or permanent offset of the diaphragm 12.

Although there has been hereinabove described a specific pressure measurement system in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A pressure measurement system comprising:
   a diaphragm having a first side and a second side;
   chamber means for exposing the diaphragm first side to a fluid;
   force transducer means for measuring force exerted by said fluid on the diaphragm first side;
   means for removably coupling said force transducer means to the diaphragm second side, said means for removably coupling comprising: (i) a ferromagnetic plate; (ii) means, extending from the diaphragm second side, for at least partially encasing a portion of said ferromagnetic plate in order to secure said ferromagnetic plate to the diaphragm second side; and (iii) magnet means, attached to said force transducer means, for removably engaging said ferromagnetic plate.

2. The system according to claim 1 wherein the means extending from the diaphragm comprises a captive portion molded into the diaphragm second side.

3. The system according to claim 2 wherein said captive portion is centered in the diaphragm second side with a surrounding resilient ring means for enabling diaphragm movement in response to a change in the force exerted on the diaphragm first side.

4. The system according to claim 3 wherein said captive portion includes a ring disposed in a spaced apart relationship with a center of said diaphragm means second side and the plate includes grove means disposed in a perimeter of the plate, for accepting said ring, said plate being firmly supported against the diaphragm means center second side by said ring.

5. The system according to claim 4 further comprising shoulder means, formed into a perimeter of said diaphragm means, for both sealing said diaphragm means to said chamber means and for tensioning said diaphragm means over an open end of said chamber means.

6. A pressure measurement system comprising:
   a diaphragm having a first side and a second side;
   chamber means for exposing the diaphragm first side to a fluid;
   force transducer means for measuring force exerted by said fluid on the diaphragm first side;
   means for removably coupling said force transducer means to the diaphragm second side, said means for removably coupling comprising, (i) a plate; (ii) means, extending from the diaphragm second side, for at least partially encasing a portion of said plate in order to secure said plate to the diaphragm second side; and (iii) latching means, disposed on said plate for removably engaging said force transducer.

7. The system according to claim 6 wherein the means extending from the diaphragm comprises a captive portion molded into the diaphragm second side.

8. The system according to claim 7 wherein said captive portion is centered in the diaphragm second side with a surrounding resilient ring means for enabling diaphragm movement in response to a change in the force exerted on the diaphragm first side.

9. The system according to claim 8 wherein said captive portion includes a ring disposed in a spaced apart relationship with a center of said diaphragm means second side and the plate includes groove means disposed in a perimeter of the plate, for accepting said ring, said plate being firmly supported against the diaphragm means center second side by said ring.

10. The system according to claim 9 further comprising shoulder means, formed into a perimeter of said diaphragm means, for both sealing said diaphragm means to said chamber means and for tensioning said diaphragm means over an open end of said chamber means.

11. In a pressure measurement system having a diaphragm, force transducer means for measuring force exerted by a fluid within a chamber and on a first side of said diaphragm, improved means for removably coupling said force transducer means to a second side of said diaphragm, the improvement comprising:
    a ferromagnetic plate;
    means, extending from the second side of the diaphragm, for at least partially encasing a portion of said ferromagnetic plate in order to secure said ferromagnetic plate to the diaphragm second side; and
    magnet means, attached to the force transducer, for removably engaging the ferromagnetic plate.

12. The improvement according to claim 11 wherein the means extending from the diaphragm comprises a captive portion molded into the diaphragm second side.

13. The improvement according to claim 12 wherein said captive portion is centered in the diaphragm second side with surrounding resilient ring means for enabling diaphragm movement in response to a change in the force exerted on the diaphragm first side.

14. The improvement according to claim 13 wherein said captive portion includes a ring disposed in a spaced apart relationship with a center of said diaphragm means second side and the plate includes a groove means disposed in a perimeter of the plate, for accepting said ring, said plate being firmly supported against the diaphragm means center second side by said ring.

15. The improvement according to claim 14 further comprising shoulder means, formed into a perimeter of said diaphragm means, for both sealing said diaphragm means to said chamber means and for tensioning said diaphragm means over an open end of said chamber means.

16. In a pressure measurement system having a diaphragm, force transducer means for measuring force exerted by a fluid within a chamber and on a first side of said diaphragm and means for removably coupling said force transducer means to a second side of said diaphragm, improved means for removably coupling said force transducer means to a second side of said diaphragm, the improvement comprising:

a plate;

means, extending from the diaphragm second side, for at least partially encasing a portion of said plate in order to secure said plate to the diaphragm second side; and latching means disposed on said plate for removably engaging said force transducer.

17. The improvement according to claim 16 wherein the means extending from the diaphragm comprises a captive portion molded into the diaphragm second side.

18. The improvement according to claim 17 wherein said captive portion is centered in the diaphragm second side with surrounding resilient ring means for enabling diaphragm movement in response to a change int he force exerted on the diaphragm first side.

19. The improvement according to claim 18 wherein said captive portion includes a ring disposed in a spaced apart relationship with a center of said diaphragm means second side and the plate includes groove means disposed in a perimeter of the plate, for accepting said ring, said plate being firmly supported against the diaphragm means center second side by said ring.

20. The improvement according to claim 19 further comprising shoulder means, formed into a perimeter of said diaphragm means, for both sealing said diaphragm means to said chamber means and for tensioning said diaphragm means over an open end of said chamber means.

\* \* \* \* \*